US012109150B2

(12) United States Patent
Kim

(10) Patent No.: US 12,109,150 B2
(45) Date of Patent: *Oct. 8, 2024

(54) OPHTHALMIC TREATMENT DEVICE, METHOD FOR CONTROLLING OPHTHALMIC TREATMENT DEVICE, AND FUNDUS LESION TREATMENT METHOD

(71) Applicant: Lutronic Vision Inc., Burlington, MA (US)

(72) Inventor: Jong Min Kim, Seoul (KR)

(73) Assignee: Lutronic Vision Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/850,987

(22) Filed: Jun. 27, 2022

(65) Prior Publication Data
US 2022/0323252 A1    Oct. 13, 2022

Related U.S. Application Data

(63) Continuation of application No. 16/569,236, filed on Sep. 12, 2019, now Pat. No. 11,382,792, which is a continuation of application No. 15/103,213, filed as application No. PCT/KR2014/012079 on Dec. 9, 2014, now Pat. No. 10,420,676.

(60) Provisional application No. 61/913,902, filed on Dec. 9, 2013.

(51) Int. Cl.
*A61F 9/008* (2006.01)

(52) U.S. Cl.
CPC .... *A61F 9/008* (2013.01); *A61F 2009/00863* (2013.01); *A61F 2009/00897* (2013.01)

(58) Field of Classification Search
CPC ............ A61F 9/008; A61F 2009/00897; A61F 2009/00863
See application file for complete search history.

(56) References Cited

U.S. PATENT DOCUMENTS

| 8,562,595 | B2 | 10/2013 | Plunkett et al. |
| 10,420,676 | B2 * | 9/2019 | Kim ........................ A61F 9/008 |
| 11,382,792 | B2 * | 7/2022 | Kim ........................ A61F 9/008 |
| 2004/0039378 | A1 | 2/2004 | Lin |
| 2006/0100677 | A1 | 5/2006 | Blumenkranz et al. |

(Continued)

FOREIGN PATENT DOCUMENTS

| JP | 2006524515 A | 11/2006 |
| JP | 2009514564 A | 4/2009 |

(Continued)

OTHER PUBLICATIONS

International Search Report for International Patent Application No. PCT/KR2014/012079 filed Dec. 9, 2014.

*Primary Examiner* — Rex R Holmes

(57) ABSTRACT

The present invention relates to an ophthalmic treatment device, a control method therefor and a fundus lesion treatment method, the ophthalmic treatment device comprising: a treatment beam generation unit for generating a treatment beam; a beam delivery unit for forming a path through which the treatment beam generated from the treatment beam generating unit is irradiated into a patient's fundus; and a control unit for controlling the beam delivery unit to irradiate the treatment beam into a location adjacent to the lesion area of the fundus.

20 Claims, 15 Drawing Sheets

(56) References Cited

U.S. PATENT DOCUMENTS

| | | |
|---|---|---|
| 2007/0129775 A1 | 6/2007 | Mordaunt et al. |
| 2010/0049173 A1 | 2/2010 | Plunkett et al. |
| 2011/0201866 A1* | 8/2011 | Cipriani ............... A61N 5/1028 600/1 |
| 2012/0165799 A1 | 6/2012 | Yamamoto |
| 2015/0366705 A1* | 12/2015 | Ha .......................... A61F 9/008 606/6 |

FOREIGN PATENT DOCUMENTS

| | | |
|---|---|---|
| JP | 2010-507412 A | 3/2010 |
| JP | 2012135550 A | 7/2012 |
| KR | 1020130035825 A | 4/2013 |

\* cited by examiner

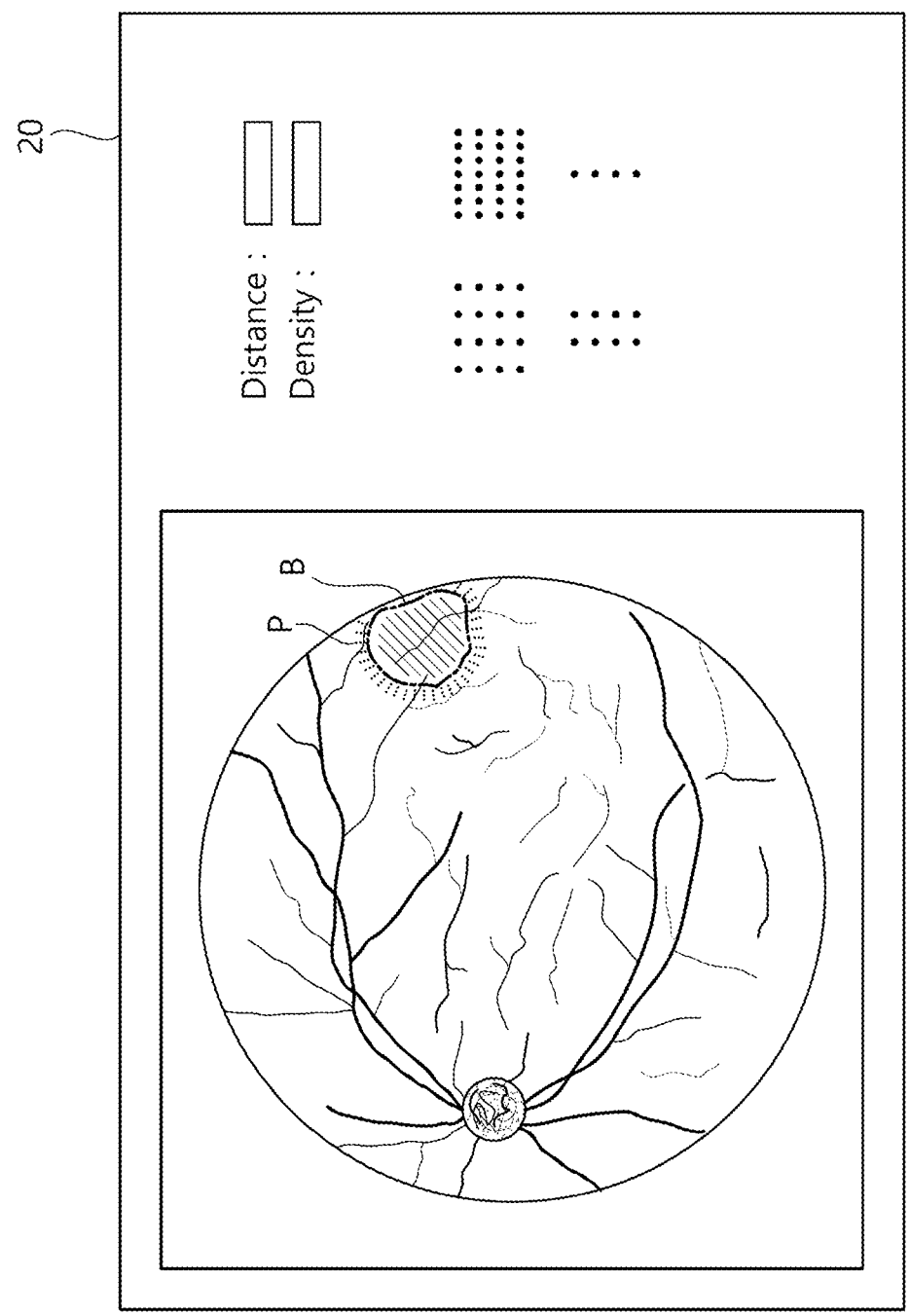

OPHTHALMIC TREATMENT DEVICE, METHOD FOR CONTROLLING OPHTHALMIC TREATMENT DEVICE, AND FUNDUS LESION TREATMENT METHOD

CROSS-REFERENCE TO RELATED APPLICATIONS

This present application is a continuation of U.S. application Ser. No. 16/569,236 filed Sep. 12, 2019, now U.S. Pat. No. 11,382,792, which is a continuation of U.S. application Ser. No. 15/103,213 filed Jun. 9, 2016, now U.S. Pat. No. 10,420,676, which is a U.S. National Stage of International Patent Application No. PCT/KR2014/012079 filed Dec. 9, 2014, which claims priority to and the benefit of U.S. Provisional Application No. 61/913,902 filed on Dec. 9, 2013, now expired, the entire contents of which are incorporated herein by reference.

TECHNICAL FIELD

The present invention relates to an ophthalmic treatment device, a method of controlling the same, and a method of treating a fundus lesion, and more particularly, to an ophthalmic treatment device, a method of controlling the same, and a method of treating a fundus lesion that can treat a fundus area by radiating light to a patient's fundus.

BACKGROUND ART

Nowadays, technology that treats with a method of changing a state of a human body tissue by light energy by radiating light that can be absorbed into the human body tissue to a human body has been widely applied. A treatment device using laser is widely used for various lesions such as skin disease, eye disease, nerve disease, joint disease, and gynecology disease.

As an ophthalmic treatment device using laser, many methods and devices for treating an anterior segment lesion of eye such as cornea surgery and glaucoma or cataract surgery have been developed, and recently, a method and device for treating various lesions of a fundus area as well as macular degeneration have been developed.

DISCLOSURE

Technical Problem

The present invention provides an ophthalmic treatment device, a method of controlling the same, and a method of treating a fundus lesion that can prevent a lesion area from additionally extending when treating a lesion of a fundus area.

Technical Solution

In accordance with an aspect of the present invention, an ophthalmic treatment device includes: a treatment beam generation unit that generates a treatment beam; a beam delivery unit that forms a path that radiates a treatment beam generated in the treatment beam generation unit to a patient's fundus; and a controller that controls the beam delivery unit to radiate the treatment beam to a location adjacent to a lesion area of the fundus.

The treatment beam may transfer energy to a depth in which an RPE cell layer is located at the patient's fundus. The lesion area of the fundus may be any one of an area in which geography antiography has occurred, an area in which drugen is formed, an area in which blood leakage (blood leakage from a new blood vessel formed in a retina base) has occurred, and an area in which macular edema is formed.

The controller may control to radiate the treatment beam along a pattern that partitions between the lesion area and the center of the fundus in order to prevent the lesion area from being extended to a central area of the fundus.

The controller may control to radiate the treatment beam along a pattern separated by a predetermined gap or more from a boundary of the lesion area. Here, a pattern of the treatment beam may be separated by 10-200 µm from a boundary of the lesion area or may be separated from a boundary of the lesion area such that 1 to 20 or more RPE cells are located between the pattern of the treatment beam and a boundary of the lesion area.

A pattern of the treatment beam may be formed in a form that encloses the lesion area in order to prevent the lesion area from being extended. Specifically, a pattern of the treatment beam may form a closed curve that encloses the lesion area at the outside of the lesion area.

The treatment beam pattern may include a first pattern and a second pattern, and the second pattern may be separately located further than the first pattern from a boundary of the lesion area. A radiation gap of a treatment beam constituting the first pattern may be smaller than that of a treatment beam constituting the second pattern.

The ophthalmic treatment device may further include a monitoring unit that radiates a probe beam to a location to which the treatment beam is radiated and that detects state information of a corresponding location based on interference information of the probe beam scattered or reflected at a location at which the treatment beam is radiated.

The controller may control to sequentially radiate at least one treatment beam at the same location and control a parameter of the treatment beam based on state information of a corresponding location detected in the monitoring unit.

In accordance with another aspect of the present invention, a method of treating a fundus lesion includes: determining a lesion area using a patient's fundus image; setting a radiation pattern of a treatment beam along a location adjacent to the lesion area; and radiating a treatment beam along the preset radiation pattern of a treatment beam.

In accordance with another aspect of the present invention, a method of controlling an ophthalmic treatment device includes: acquiring a fundus image including lesion area information; and setting a pattern in which a treatment beam is radiated along a location adjacent to the lesion area.

Advantageous Effects

According to the present invention, by regenerating an RPE cell of an adjacent area by radiating light to an area adjacent to a lesion area, the lesion area can be effectively prevented from being extended.

BRIEF DESCRIPTION OF THE DRAWINGS

FIG. 11 is a diagram illustrating a display content of a display unit that sets treatment contents of FIG. 10.

BEST MODE

Figure 1:
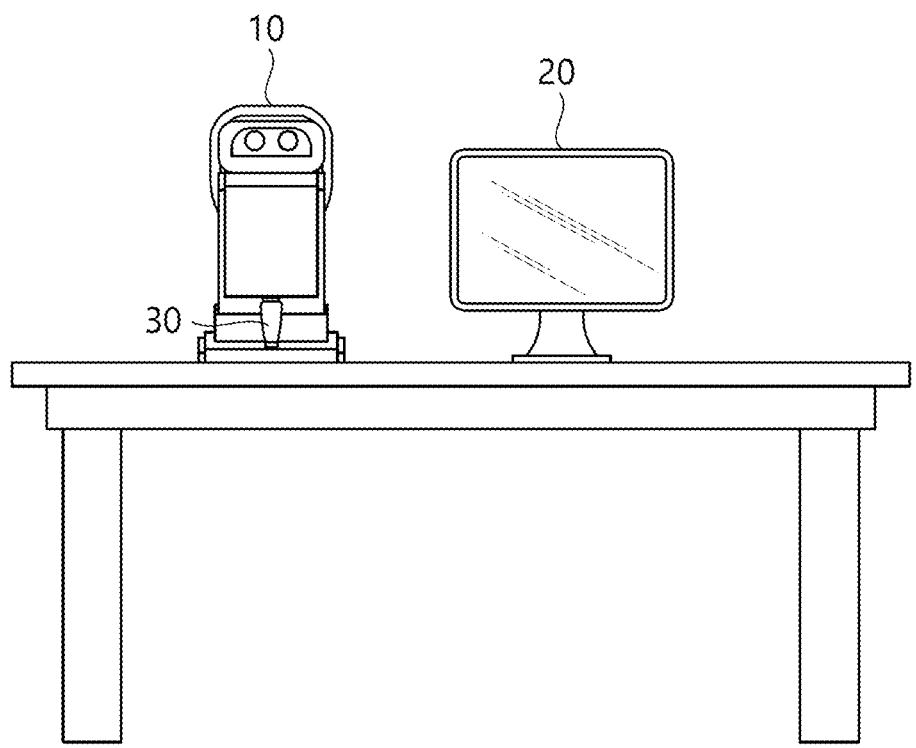
FIG. 1 is a perspective view illustrating an ophthalmic treatment device according to an exemplary embodiment of the present invention.

Hereinafter, an ophthalmic treatment device according to an exemplary embodiment of the present invention will be described in detail with reference to the drawings. In the following description, a location relationship of each element will be described based on the drawing. For convenience of description, the drawing may simplify a structure of the invention or may be exaggeratingly displayed, as needed. Therefore, the present invention is not limited thereto and various devices may be added to the present invention, or elements of the present invention may be changed or omitted.

In the present exemplary embodiment, an ophthalmic treatment device for treating a lesion of a fundus area such as a retina and a method of treating a fundus lesion using the same are described as an example, but the present invention is not limited to the following configuration or step.

Figure 2:
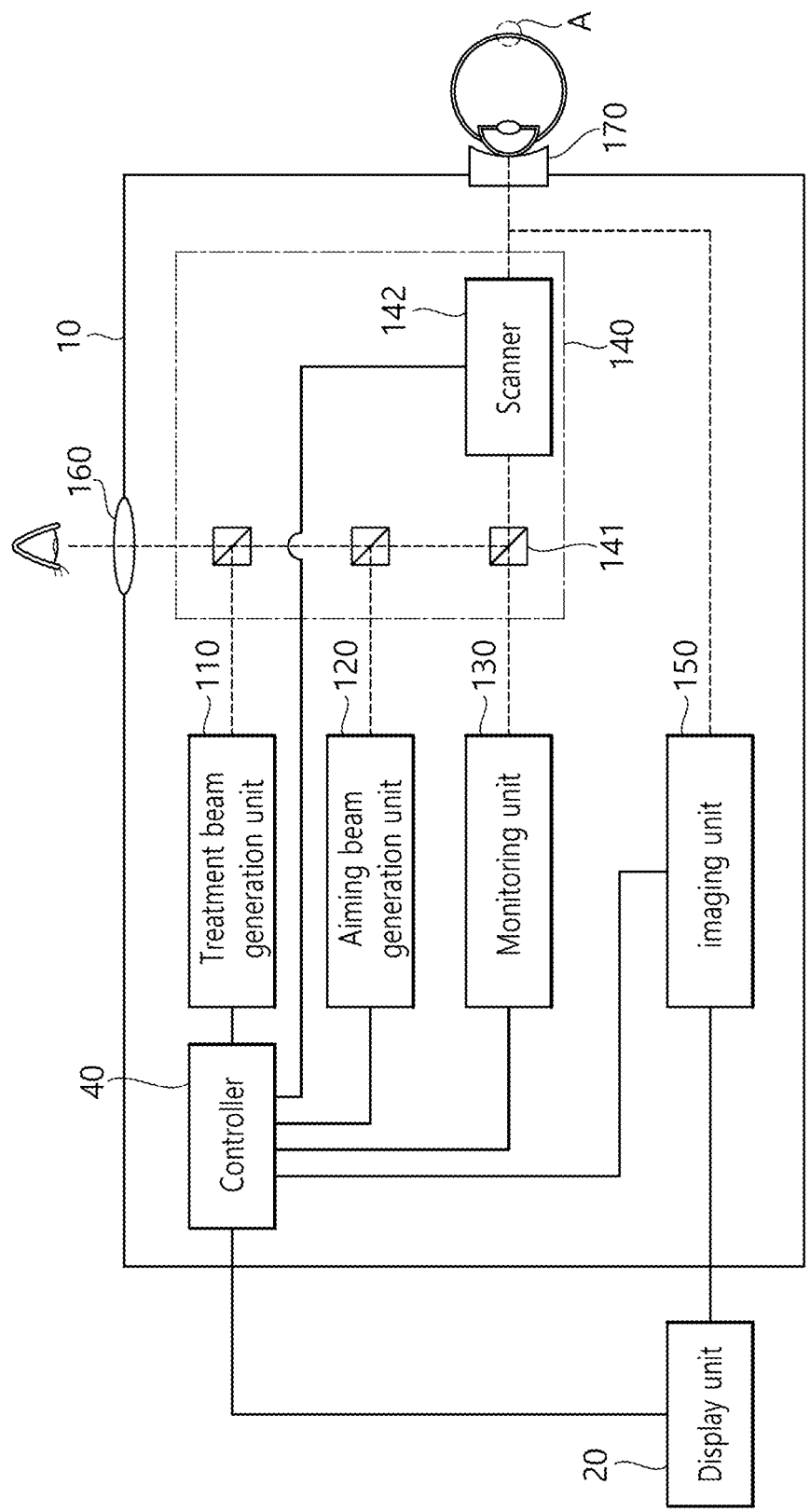
FIG. 2 is a schematic diagram illustrating the ophthalmic treatment device of FIG. 1.

FIG. 1 is a perspective view illustrating an ophthalmic treatment device according to an exemplary embodiment of the present invention and FIG. 2 is a schematic diagram illustrating the ophthalmic treatment device of FIG. 1. As shown in FIG. 1, an ophthalmic treatment device according to the present exemplary embodiment may include a slit lamp 10 and a display unit 20.

The slit lamp 10 is a device that enables an operator to treat while observing a patient's eye. At one side of a main body of the slit lamp 10, an object part 170 for fixing a patient's eye location is provided, and at the other side thereof, an eyepiece part 160 that enables an operator to observe a patient's eye is provided. At the outside of the slit lamp 10, various manipulation units 30 for adjusting treatment contents or a visual field direction in which the operator observes may be provided. At the inside of the slit lamp 10, various constituent elements may be housed.

As shown in FIG. 2, the slit lamp 10 may include a treatment beam generation unit 110 that generates a treatment beam, an aiming beam generation unit 120 that generates an aiming beam, and a beam delivery unit 140 that forms a path in which the treatment beam and the aiming beam advance to the patient's fundus. The slit lamp 10 may further include a monitoring unit 130 for detecting state information of a radiation location of a treatment beam while treating, a imaging unit 150 for acquiring the patient's fundus image, and a controller 40 for controlling operation of the foregoing various constituent elements.

The treatment beam generation unit 110 may include a treatment beam light source (not shown) that generates a treatment beam and various optical elements for adjusting a parameter of a treatment beam generated in the treatment beam light source.

For example, the treatment beam light source may include a laser medium or a laser diode such as Nd:YAG and Ho:YAG that can oscillate laser. In a treatment beam generated in the treatment beam light source, a parameter may be adjusted by various optical elements such as an optical filter, an optical lens, and a shutter or various electric circuits for exciting a laser medium. Here, a parameter of a treatment beam may be at least one of an output magnitude of a treatment beam, a beam size at a radiation location, and a pulse pattern such as a pulse width or a pulse cycle. However, a portion of a parameter of a treatment beam may be adjusted by the beam delivery unit.

A treatment beam generated in the treatment beam generation unit 110 selectively provides energy to a specific location or a specific tissue to be a treatment target among fundus retina tissues formed in a multiple layer structure. Therefore, a treatment beam is formed using laser having a wavelength or a pulse width having low absorbancy in another tissue and high absorbancy in a target tissue. The treatment beam generation unit 110 of the present exemplary embodiment may generate light of a wavelength that may be selectively absorbed into an RPE cell layer in a retina tissue and generate laser of, for example, a wavelength of 500 nm-600 nm or 800 nm-900 nm.

The aiming beam generation unit 120 generates an aiming beam radiated to a treatment area. Before a treatment beam is radiated or while a treatment beam is radiated, an aiming beam notifies an operator of a location at which a treatment beam is radiated and is directly radiated to the patient's fundus. Such an aiming beam has a wavelength of a visible ray band such that an operator directly determines through an eyepiece part.

An aiming beam generated in the aiming beam generation unit 120 may be radiated in a single spot form in order to display one target location at which a treatment beam is radiated and may be radiated in a plurality of spot forms in order to simultaneously display a plurality of locations in which a treatment beam is sequentially radiated. In addition, an aiming beam may be radiated in a lattice form and may be radiated with various methods such as a display of a boundary of an area in which a treatment beam is radiated.

FIG. 1 illustrates a configuration that enables the aiming beam generation unit 120 to radiate an aiming beam through the same path as that of a treatment beam through the beam delivery unit 140, but the aiming beam generation unit 120 may have a light path separate from that of a treatment beam. Further, when the operator can determine a location at which a treatment beam is radiated through a separate interface (e.g., a display unit), the aiming beam generation unit may be omitted.

The beam delivery unit 140 is formed with a plurality of optical elements disposed between the treatment beam generation unit 110 and the object part 170 and forms a light path in which a treatment beam, an aiming beam and/or a probe beam of a monitoring unit to be described later advance.

Specifically, as shown in FIG. 1, the beam delivery unit 140 has a plurality of beam combiners 141. Thereby, a treatment beam generated in the treatment beam generation unit, an aiming beam generated in the aiming beam generation unit, and a probe beam to be generated in the monitoring unit 130 to be described later may enter the beam delivery unit 140 to be transferred to a target location along a common path. An aiming beam and probe beam reflected from the target location may advance backward a radiated path to advance in a direction of the eyepiece part 160 or to the monitoring unit 130 along the beam delivery unit.

Such a beam delivery unit 140 may include a scanner 142 that changes a location at which a treatment beam, an aiming beam, and a probe beam are radiated on a light path. The scanner may include at least one reflection mirror and a driver that rotates the at least one reflection mirror. The driver changes an angle of a reflection mirror that reflects light and thus changes a radiation location of each light.

Further, although not specifically shown in the drawing, the beam delivery unit 140 may further include optical elements such as a plurality of optical filters and optical lenses for focusing or distributing light.

In an end portion of the beam delivery unit, an object part 170 is provided. The object part 170 is a portion in which a patient locates his eye and may include a contact lens that contacts with the patient's eye. Further, in order to fix the patient's eye while operating, the ophthalmic treatment device may include a suction device that inhales and fixes the patient's eye.

Figure 3:
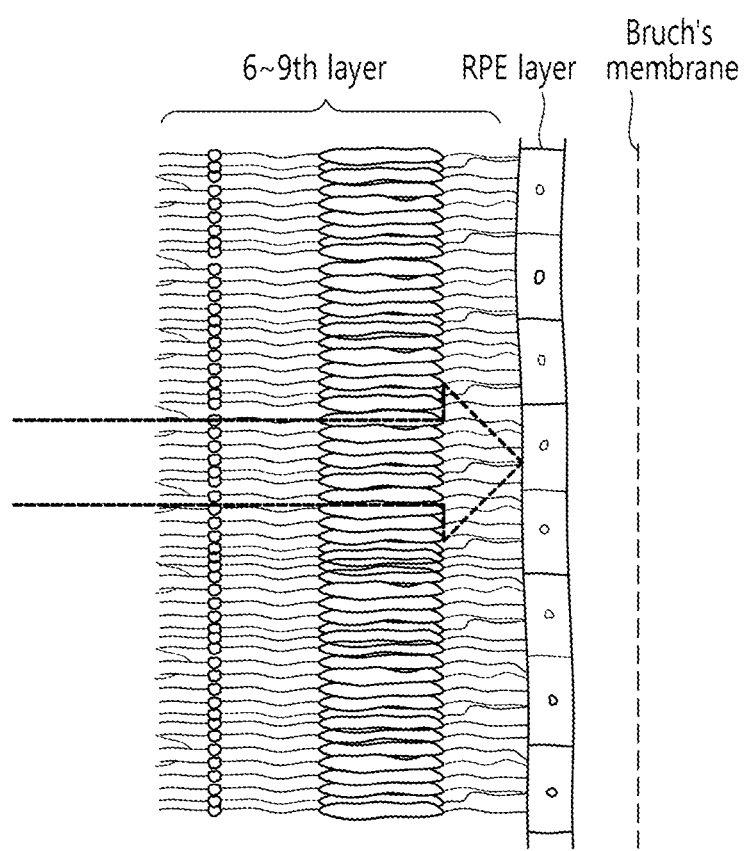
FIG. 3 is a diagram illustrating a retina tissue corresponding to a patient's fundus.

FIG. 3 is a diagram illustrating a retina tissue corresponding to a patient's fundus and is an enlarged cross-sectional view of an area A of FIG. 1. The retina tissue of a fundus is generally formed with 10 layers of an internal limiting layer, a nerve fiber layer, a ganglion cell layer, an inner plexiform layer, an inner nuclear layer, an outer plexiform layer, an outer nuclear layer, an external limiting layer, a photo receptor layer, and a retinal pigment epithelial layer (RPE layer) (an inner depth direction from a retina surface).

The RPE cell layer (retinal pigment epithelial) forms a boundary layer of a backward direction of the retina among the 10 layers and is formed in a tight junction structure. In a lower portion of the RPE layer, a Bruch's membrane is located. Such an RPE layer performs a function of receiving nutrients and oxygen from a blood vessel located at a lower portion of a choroid coat to supply the nutrients to a photo receptor and discharging wastes generated in the photo receptor through the Bruch's membrane.

However, when a portion of an RPE cell forming the RPE layer does not perform a normal function, photo receptors of a location corresponding to the RPE cell die because nutrients or oxygen is not normally supplied. Therefore, the ophthalmic treatment device according to the present exemplary embodiment radiates a treatment beam to an RPE cell layer that does not perform a normal function to apply energy and thus induces a new RPE cell to regenerate at a corresponding location, thereby performing a treatment.

In more detail, as described above, a treatment beam generated in the treatment beam generation unit 110 has a wavelength of a visible ray or near infrared ray area. Light of such a wavelength is not almost absorbed but transmitted at a cell layer (a first cell layer to a ninth cell layer) located at the front side of the retina and is absorbed into melanosomes existing within a cell of the RPE cell layer. Therefore, as an amount of energy absorbed by a treatment beam increases, a state of an RPE cell changes and thus a treatment is performed with a method of regenerating a new RPE cell. It is analyzed that the treatment is performed as follows. As a temperature of melanosome rises, a micro bubble occurs at a surface of melanosome, and as the micro bubble gradually grows, an RPE cell selectively dies, and an adjacent RPE cell regenerates a healthy RPE cell at a corresponding location through division and movement.

In this case, when an excessively large amount of treatment beam is radiated, an adjacent RPE cell or an adjacent photo receptor cell as well as an RPE cell to be a treatment target may be thermally damaged. Therefore, in the present exemplary embodiment, the ophthalmic treatment device may include the monitoring unit 130 for monitoring treatment contents while treating.

Specifically, while a treatment beam is radiated, the monitoring unit 130 may monitor in real time state information of a target tissue of a location at which the treatment beam is radiated. Here, state information may include at least one of information about a temperature change, a volume change, and a refractive index change of a tissue of a corresponding location, and a cell movement or a signal generated due to the change and movement. Such a monitoring unit 130 may be formed in various structures for detecting such state information at a corresponding location.

For example, the monitoring unit 130 according to the present exemplary embodiment may detect state information of a tissue by interference information of light, as in an optical coherent tomography (OCT) device. The OCT device generally divides one beam into a probe beam and a reference beam and advances the beam along a separate path and again combines and receives the probe beam reflected from a target location with the reference beam, and in this time, the OCT device acquires a tomographic image based on interference information of two beams.

The monitoring unit 130 of the present exemplary embodiment may separately have a path in which a probe beam and a reference beam advance, as in the OCT device. In this case, a reference beam advances along a preset path, and a probe beam is radiated and reflected to a target location along a path in which a treatment beam advances through the beam delivery unit 140 to be received to the monitoring unit 130. A detection unit (not shown) of the monitoring unit 130 may detect interference information between a received reference beam and probe beam.

However, a conventional OCT device acquires a (coordinate on a plane vertical to a path of a probe beam, B-scan) tomographic image while moving a horizontal direction coordinate, however the monitoring unit 30 according to the present exemplary embodiment detects in real time a state information change of a tissue while radiating a probe beam multiple times to a corresponding location while a treatment is performed at one location (performs a treatment of a corresponding location while a plurality of treatment beams are radiated to one location). Specifically, as a treatment beam is radiated, when a predetermined amount or more of energy is absorbed into a target location, a tissue is deformed and thus while a light transmitting characteristic, a scattering characteristic, and a reflection characteristic of a corresponding tissue change, a path characteristic in which a probe beam advances is changed. When an advancing path characteristic of the probe beam is changed, interference information detected in the monitoring unit 130 is also changed and thus at a time point in which the interference information changes, it may be detected that a tissue state is changed by a treatment beam.

Interference information obtained in the monitoring unit 130 may include various information, and in the present exemplary embodiment, as an example, information corresponding to a depth area of a target location is extracted among speckle pattern information obtained from interference information, by continuously comparing a change amount of each extracted information, a state change of a tissue may be detected.

However, the foregoing configuration of the monitoring unit is an example, and the monitoring unit may detect state change information of a tissue using an optical method, as in a fundus camera and detect a signal generated due to a state change of a tissue when radiating a treatment beam using a sound wave sensor, a ultrasonic wave sensor, and a temperature sensor and may be variously changed.

Before a treatment starts or while a treatment performs, the imaging unit 150 obtains the patient's fundus image. The obtained fundus image may be displayed to the operator through the display unit 20 or may be stored at a separate database. The imaging unit 150 radiates an imaging beam to the patient's fundus and acquires an image using a reflected beam. Therefore, although not specifically shown in the drawing, the imaging unit 150 may include a imaging light source, an optical element forming a light path, and an image pickup element that acquires an image from a reflected imaging light. In this case, a imaging beam generated in the imaging light source may form a light path using the foregoing beam delivery unit and may form a separate light path.

The display unit 20 is provided at a location adjacent to the slit lamp 10 to display various information necessary for the operator while treating. As shown in FIG. 1, the display unit 20 may be formed using a flat display device and may be formed using various display devices. Alternatively, the display unit 20 may be formed with a head-up display within the slit lamp or may be provided at various locations for the operator's convenience.

Such a display unit 20 displays a patient's fundus image through a display. Such a fundus image may be input by a separate diagnosis device and may be displayed using a fundus image obtained in the imaging unit. A fundus image displayed in the display unit 20 includes a patient's lesion area information, and the operator may determine a lesion area using a fundus image displayed in the display unit 20.

Further, the operator may set various parameters of a treatment beam and operation contents of various constituent elements within the slit lamp as well as a pattern in which a treatment beam is radiated using the display unit 20. For this reason, a display of the display unit 20 may be formed with a touch screen, and various input devices such as a mouse and a keyboard may be connected thereto. Therefore, the operator may set treatment contents through an input device with reference to a fundus image displayed in the display unit.

The controller 40 may control operation of various constituent elements such as the treatment beam generation unit 110, the aiming beam generation unit 120, the monitoring unit 130, the beam delivery unit 140, and the scanner 142 according to an operation signal input by the operator through a manipulation unit or a display unit.

For example, when the operator sets a radiation pattern of a treatment beam through the display unit 20, the controller 40 may control various constituent elements to radiate a treatment beam to correspond to a corresponding pattern. Alternatively, the controller 40 may control to adjust a parameter of a treatment beam according to the operator's setting or a previous input mode through the display unit 20.

Further, the controller 40 may control operation of the treatment beam generation unit 110 based on state information of a target location detected in the monitoring unit 130. Until a tissue change (e.g., dead of an RPE cell) at one target location is detected, the ophthalmic treatment device according to the present exemplary embodiment radiates a treatment beam multiple times to perform a treatment. Therefore, while a treatment beam is radiated multiple times at one target location, the monitoring unit 130 radiates a probe beam multiple times to correspond to a treatment beam to detect state information of a treatment location and determines whether state information is changed. Here, while treating, the controller 40 may control a parameter of a treatment beam or whether to stop radiation of a treatment beam based on state information of a corresponding location detected in the monitoring unit 130. Specifically, the controller 40 controls the treatment beam generation unit 110 to sequentially transfer high energy from lower energy at one location. When it is detected that state information is changed at a corresponding location through the monitoring unit 130, an increase amount of transferred energy may be lowered or radiation of a treatment beam may be stopped. The controller controls to transfer energy approaching a threshold point in which a state change occurs at each location with such a method, thereby preventing an adjacent tissue from being damaged with excessive radiation of a treatment beam.

FIGS. 4A to 4E are graphs illustrating an example of a parameter change of a treatment beam adjusted by a controller. As described above, by controlling to sequentially transfer high energy to one location, the controller 40 may control a parameter of a treatment beam with various methods.

Figure 4A:
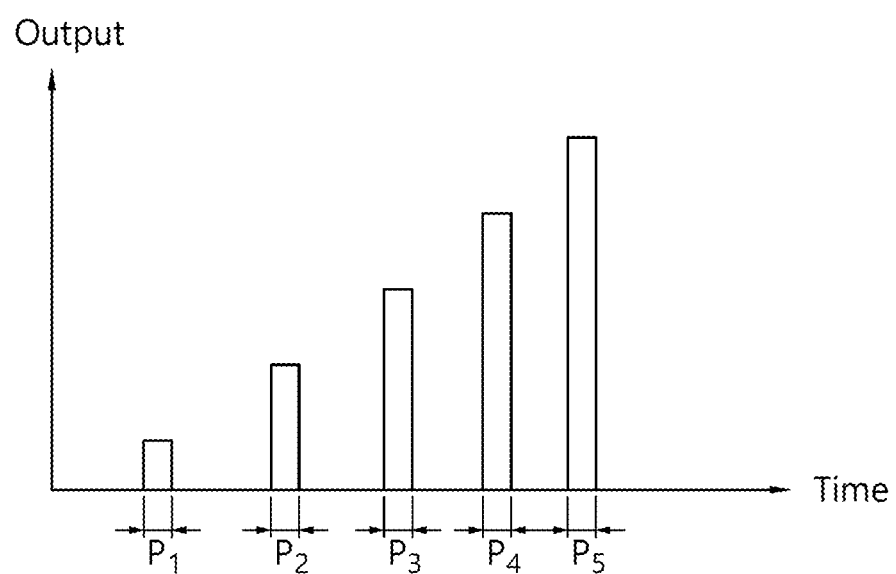
FIGS. 4A to 4E are graphs illustrating an example of a parameter change of a treatment beam adjusted by a controller.
Figure 4B:
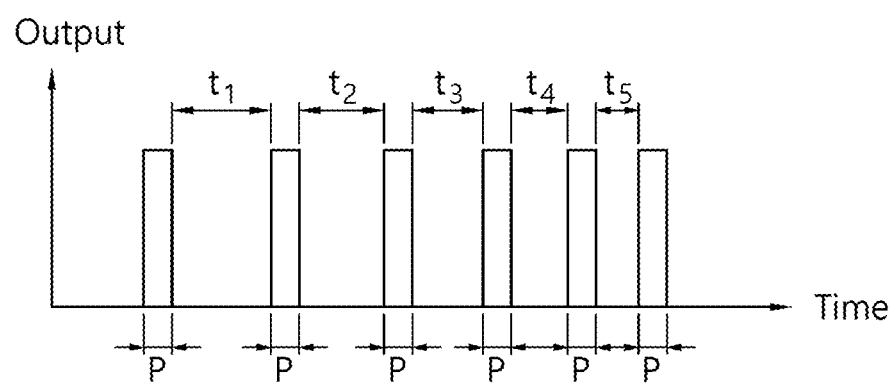
Figure 4C:
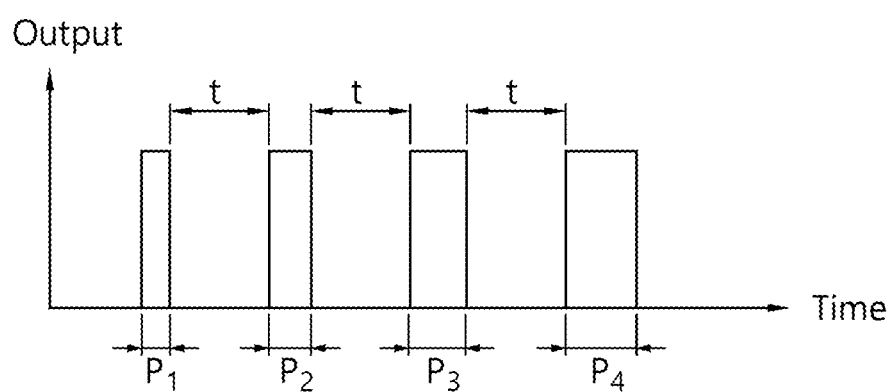
Figure 4D:
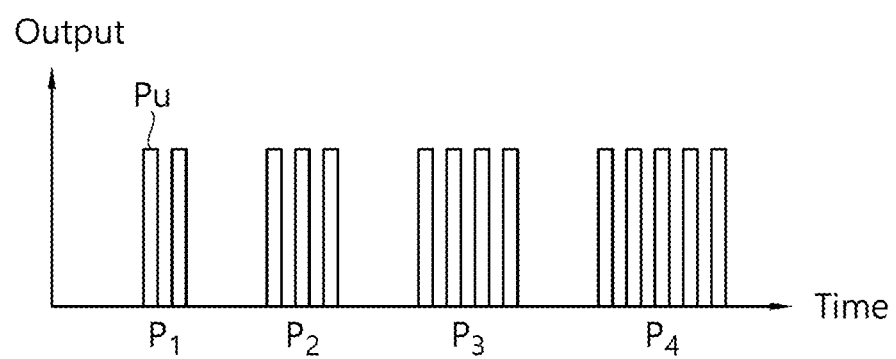
Figure 4E:
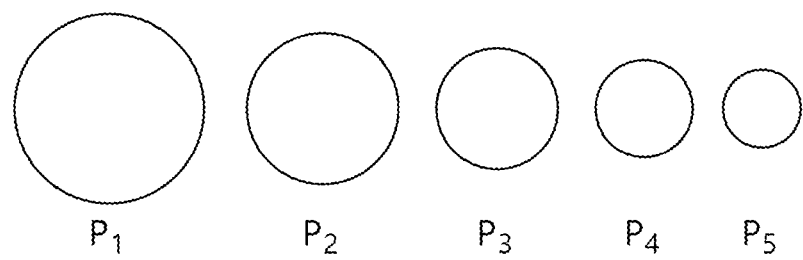

As shown in FIG. 4A, by gradually increasing an output of a treatment beam, energy transferred to a treatment location may sequentially increase. As shown in FIG. 4B, an off time between treatment beam pulses may be adjusted to gradually shorten, and as shown in FIG. 4C, a pulse duration time of a treatment beam pulse may be adjusted to gradually increase. In addition, as shown in FIG. 4D, one pulse of a treatment beam is radiated with a plurality of unit pulses having the same output, but a magnitude of transferred energy per unit area of a treatment area may sequentially increase with a method of sequentially increasing the number of a unit pulse constituting one pulse or gradually focusing a treatment beam, as shown in FIG. 4E.

In this way, the controller 40 may adjust a parameter of a treatment beam while treating using a value detected by the monitoring unit 130 and control operation of each constituent element while treating based on contents input by an operator or a preset mode.

Various lesion areas occurring in a patient's fundus tissue may be treated using such an ophthalmic treatment device. Here, the lesion area may include any one of an area in which geography antiography has occurred, an area in which drugen is formed, an area in which blood leakage has occurred, and an area in which macular edema is formed, and hereinafter, for example, a lesion area in which geography antiography has occurred will be mainly described.

Figure 5:
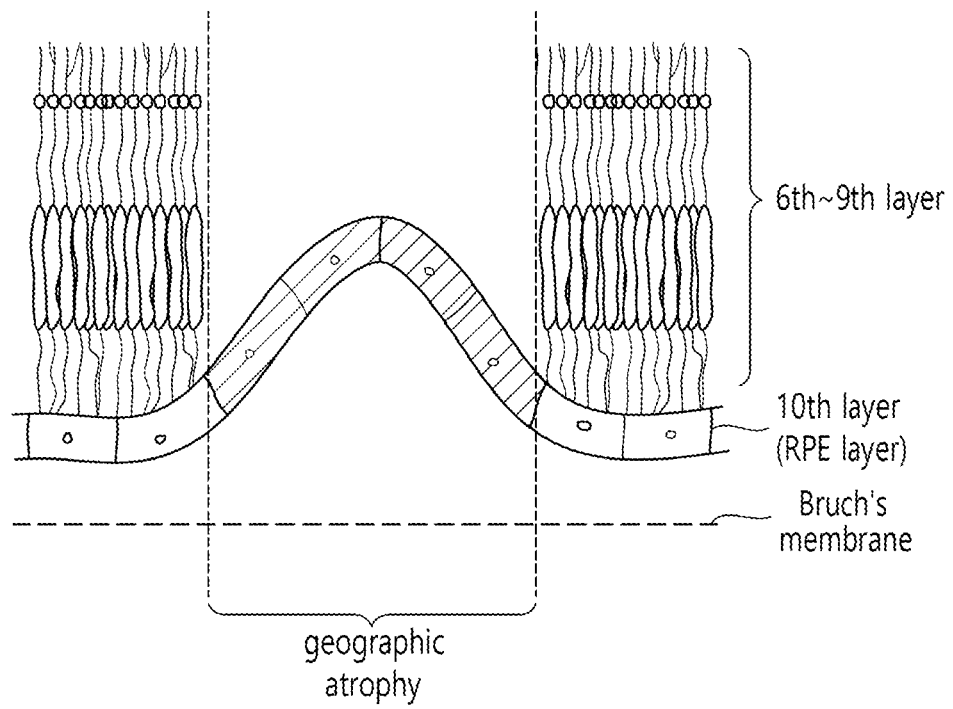
FIG. 5 is a cross-sectional view illustrating a geography antiography area that has occurred in a retina tissue.

FIG. 5 is a cross-sectional view illustrating a geography antiography area that has occurred in a retina tissue. As described above, when a portion of an RPE cell of a fundus does not perform a normal function, nutrient supply or oxygen supply is not normally performed in photo receptors of a corresponding location and thus the photo receptors die. Therefore, in such an area, a geographic atrophy phenomenon is observed. Photo receptors died in a geographic atrophy area cannot be recovered, and when an atrophy area is extended, a patient may lose eye sight.

Therefore, when such a lesion area is observed, by radiating a treatment beam, a treatment for preventing a corresponding lesion area from extending to an adjacent portion may be performed. In this case, a used treatment beam may use laser having a wavelength of 500-600 nm or 800-900 nm, and a treatment beam advances to a depth in which an RPE cell is located to selectively provide energy to an RPE cell of a corresponding location, thereby regenerating the RPE cell.

Figure 6:
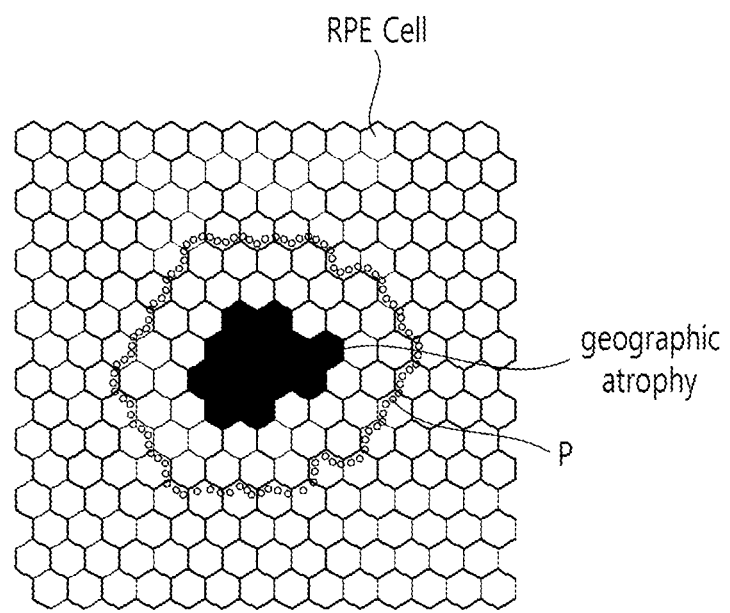
FIG. 6 is a diagram illustrating a first example of a radiation pattern of a treatment beam radiated to a lesion area.

FIG. 6 is a diagram illustrating a first example of a radiation pattern of a treatment beam radiated to a lesion area. By directly radiating a treatment beam to the lesion area according to lesion contents, regeneration of an RPE cell may be induced. However, even if a treatment beam is directly radiated to a lesion area in which the RPE cell and a photo receptor of a corresponding tissue are already died due to geographical atrophy, a treatment effect cannot be expected. In this case, as shown in FIG. 6, by radiating a treatment beam in a form that encloses the lesion area to a tissue located at the outside of the lesion area, but adjacent to a boundary of the lesion area, regeneration of an RPE cell of an adjacent portion may be induced. Thereby, even if an RPE cell is adjacent to the lesion area, the RPE cell and a photo receptor of a corresponding area can maintain a normal state, and by enhancing a health state of an tissue adjacent to the lesion area, the lesion area may be blocked from being extended, and as the RPE cell divides and regenerates to the boundary side of the lesion area, a treatment of the lesion area can be expected.

In FIG. 6, a radiation pattern P of a treatment beam may be formed in a closed curve form that encloses a lesion area. Here, when a treatment beam radiation pattern forms a closed curve, this is not limited to a case in which radiation locations of a treatment beam form a closed curve by overlapping and includes a case of forming a closed curve by connection of an adjacent radiation location of each treatment beam.

Further, it is unnecessary that a treatment beam radiation pattern is always a closed curve, and when a lesion area is located at an edge of the fundus, a treatment beam pattern may be formed in a form that crosses and partitions between a lesion area and the center (yellow spot) of the fundus. In this case, a lesion area may be blocked from extending in a central direction of the fundus.

Further, in the drawing, a treatment beam radiation pattern forms one line, but may form a plurality of lines.

Figure 7:
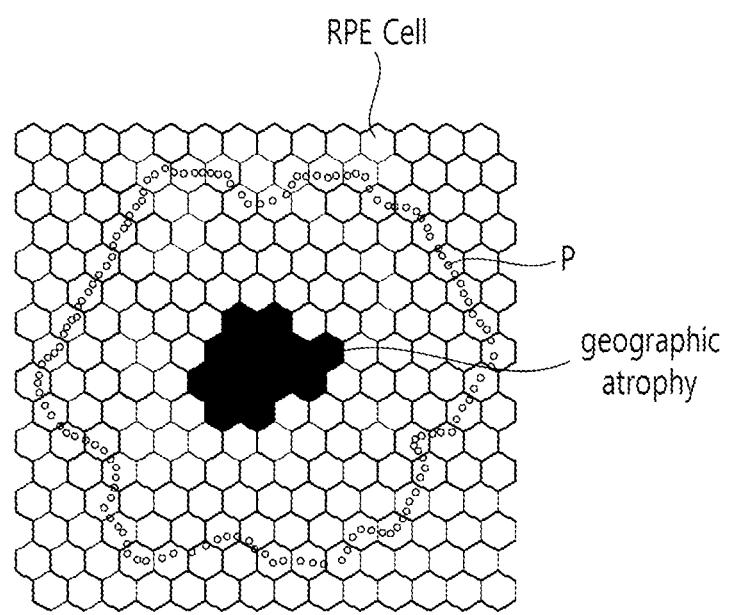
FIG. 7 is a diagram illustrating a second example of a radiation pattern of a treatment beam radiated to a lesion area.

FIG. 7 is a diagram illustrating a second example of a radiation pattern of a treatment beam radiated to a lesion area. The pattern of FIG. 7 illustrates a form in which a treatment beam is radiated to a location separated by a predetermined gap or more from a boundary of a lesion area, compared with the pattern of FIG. 6.

As described above, a treatment beam is radiated, but when an RPE cell dies, a regeneration process of the RPE cell is performed with a method of moving or dividing an adjacent RPE cell. However, in the lesion area and a portion very adjacent to the lesion area, because healthy RPE cells are relatively insufficient, regeneration of the RPE cells may not be relatively actively performed.

Therefore, as shown in FIG. 7, a radiation pattern P of a treatment beam may be formed with separated by a predetermined gap or more from a boundary of a lesion area. For example, the radiation pattern P of a treatment beam may be formed with separated by 10 μm or more from a boundary of the lesion area. However, in order not to be excessively separated from the lesion area, the treatment beam may be radiated to separate from a range of approximately 10-200 μm. Alternatively, the radiation pattern P of a treatment beam may be formed to be separated by at least one RPE cell size such that at least one RPE cell is disposed between the radiation pattern of the treatment beam and a boundary of the lesion area. However, even in this case, in order not to be excessively separated from the lesion area, the treatment beam may be radiated to a range of approximately 1 to 20 RPE cell gaps.

Figure 8:
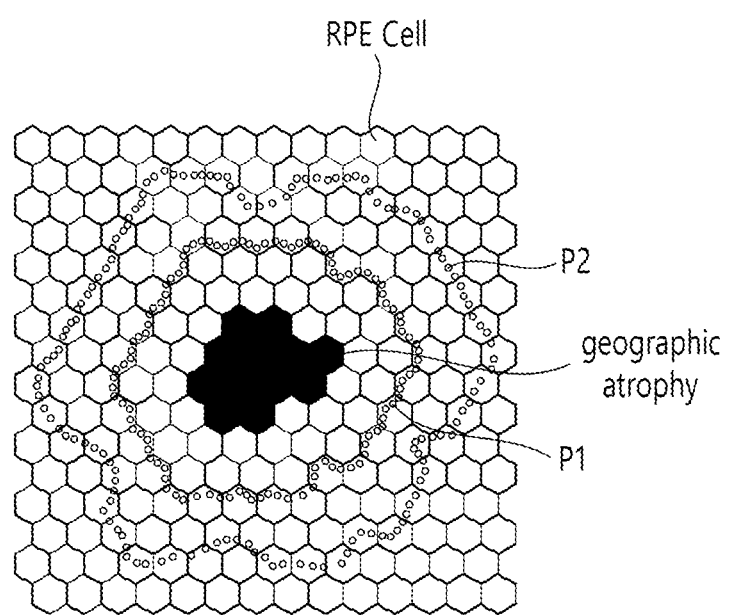
FIG. 8 is a diagram illustrating a third example of a radiation pattern of a treatment beam radiated to a lesion area.

FIG. 8 is a diagram illustrating a third example of a radiation pattern of a treatment beam radiated to a lesion area. As shown in FIG. 8, a pattern P of a treatment beam may include a first pattern P1 formed along a location adjacent to the lesion area and a second pattern P2 further separated from a boundary of the lesion area than the first pattern. In this way, a treatment beam pattern may be formed with at least two pattern combinations. In this case, in the first pattern P1 formed at a location more adjacent to a boundary of the lesion area, a radiation gap of a treatment beam constituting the first pattern may be smaller than that of a treatment beam constituting the second pattern P2.

Figure 9:
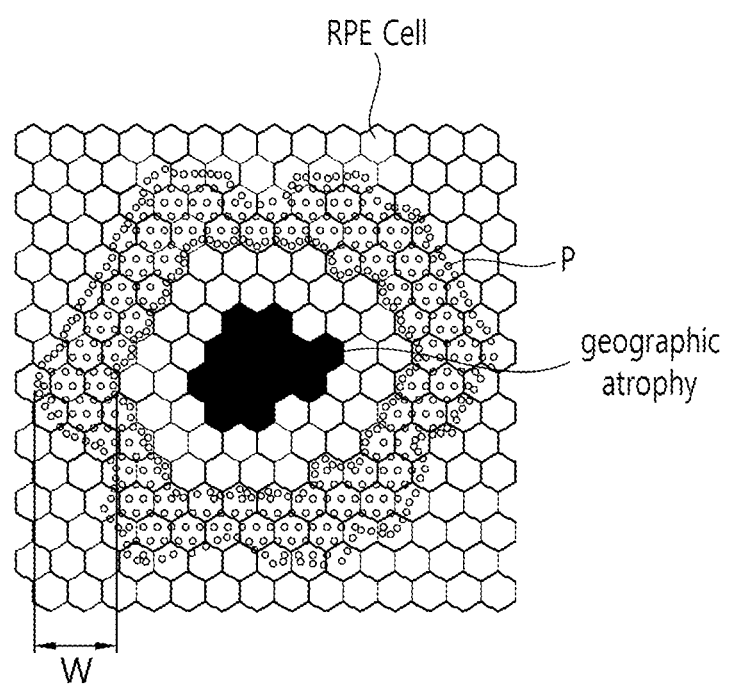
FIG. 9 is a diagram illustrating a fourth example of a radiation pattern of a treatment beam radiated to a lesion area.

FIG. 9 is a diagram illustrating a fourth example of a radiation pattern of a treatment beam radiated to a lesion area. FIGS. 6 to 8 illustrate a radiation pattern of a treatment beam radiated in a line form, but as shown in FIG. 9, a treatment beam radiation pattern P may form an area formed along a circumference of the lesion area with a predetermined width w. In this case, a width of the treatment beam radiation pattern and a spot density of a treatment beam per unit area of the treatment beam radiation pattern may be variously adjusted.

A radiation pattern of a treatment beam of FIG. 9 may be formed to be separated by a predetermined distance from a boundary of the lesion area. As shown in FIG. 7, a radiation pattern of a treatment beam may be formed to be separated by a range of 10 μm-200 μm from a boundary area or by a range of 1 to 20 RPE cell gaps based on an RPE cell gap. However, such a separation distance means a shortest distance between a radiation pattern of a treatment beam and a boundary of the lesion area, and it does not mean that a radiation location of an entire treatment beam forming a pattern should exist within the range.

In the foregoing description, various radiation patterns of a treatment beam according to the present exemplary embodiment has been described with reference to FIGS. 6 to 9, but the present invention is not limited thereto and a treatment beam may be radiated using various patterns.

Figure 10:
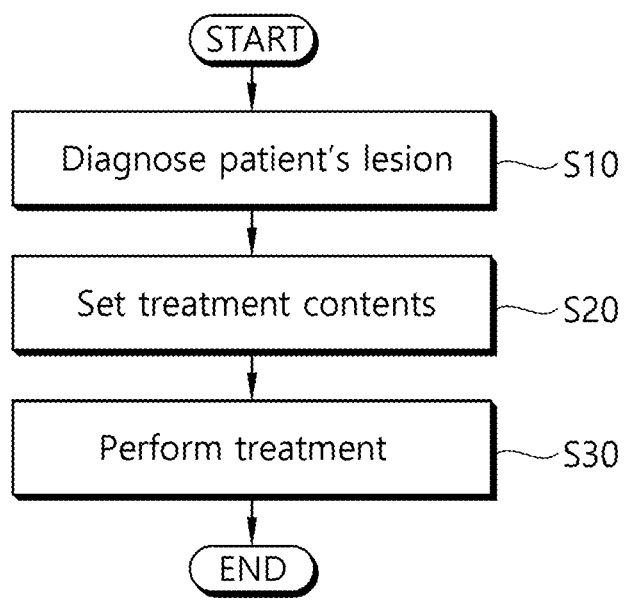
FIG. 10 is a flowchart illustrating a method of treating a fundus lesion using the ophthalmic treatment device of FIG. 1.

FIG. 10 is a flowchart illustrating a method of treating a fundus lesion using the ophthalmic treatment device of FIG. 1. Hereinafter, a method of treating a fundus lesion using the foregoing ophthalmic treatment device will be described in detail with reference to FIG. 10.

In order to treat a fundus lesion, a patient's lesion is diagnosed (S10). At this step, a fundus image including information about the patient's lesion area may be used. Such a fundus image may be an image photographed by a separate diagnosis device such as a fundus camera. Alternatively, such a fundus image may be an image obtained by the imaging unit 150 of the foregoing ophthalmic treatment device. In order to perform this step, the display unit 20 of the ophthalmic treatment device may operate to receive an input of a fundus image from the outside or the imaging unit and to display the fundus image. Therefore, the operator may determine a size and location of a lesion area in which geography antiography, drugen deposition, blood leakage, and macular edema have occurred with reference to a fundus image displayed in the display unit 20.

A lesion of the patient is diagnosed, and treatment contents may be set using the ophthalmic treatment device (S20). At this step, a radiation pattern of a treatment beam and a parameter of a treatment beam are set.

As described above, in the present exemplary embodiment, because a treatment is performed with a method of radiating a treatment beam to a location adjacent to a lesion area, a radiation pattern of a treatment beam may be formed at a location adjacent to a boundary of the lesion area, but separated by a predetermined gap or more.

Step of setting a pattern of a treatment beam may be performed by a user using a fundus image displayed in the display unit 20 (see FIG. 11). For example, when the user displays a boundary B of a lesion area on a fundus image displayed in the display unit 20, a processor (not shown) of the display unit may automatically calculate and display a radiation pattern of the treatment beam based on the boundary information. Alternatively, when an operator inputs/selects information such as a separation distance, a width of an area in which a treatment beam is radiated, and a spot density in an area in which a treatment beam is radiated among a radiation pattern of the treatment beam, the processor may calculate a treatment beam radiation pattern satisfying a corresponding condition and display the treatment beam radiation pattern in the display unit 20.

A treatment beam radiation pattern may be set at a location separated by a predetermined gap or more from a lesion area in consideration of a location and lesion contents of a lesion area with such a method. In addition, at this step, various parameters such as an output, a pulse type, and a beam size of a treatment beam may be set.

When setting of treatment contents is complete, a treatment is performed by driving the ophthalmic treatment device (S30). At this step, the controller 40 may receive a treatment beam radiation pattern coordinate calculated in a processor to drive various constituent elements in order to radiate a treatment beam to a corresponding location. At this step, the treatment beam is radiated to a plurality of locations having a separation distance (e.g., a range of 10 μm-200 μm or a range of 1 to 20 cell gaps based on an RPE cell gap) by a predetermined gap or more from a boundary of the lesion area at the outside of the lesion area according to a preset radiation pattern. At each location, a plurality of treatment beams and probe beams are radiated and thus a tissue of a corresponding location may be treated until state information changes.

A treatment is performed with such a method, i.e., a method of changing state information of a tissue by radiating a treatment beam to an area adjacent to a lesion area according to a preset pattern and thus by regenerating an RPE cell of a corresponding area, a lesion area can be treated or a lesion area can be prevented from extending.

In the foregoing description, before performing a treatment, the treatment has been performed with a method of previously setting a radiation pattern of a treatment beam and automatically radiating a treatment beam to a corresponding location. However, instead of previously setting a radiation pattern of a treatment beam, a user may perform a treatment while moving a radiation location of a treatment beam with a predetermined pattern to a location adjacent to a lesion area, but separated by a predetermined gap while determining a lesion area of a fundus through a slit lamp.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A treatment device, comprising:
a treatment beam generation unit generating a treatment beam;
a beam delivery unit delivering the treatment beam generated in the treatment beam generation unit to a patient's treatment area; and
a controller controlling at least one of the treatment beam generation unit and a beam delivery unit to radiate the treatment beam to one or more locations adjacent to a lesion area of the treatment area without radiating the treatment beam to the lesion area, the one or more locations being outside the lesion area and separated from a boundary of the lesion area so as to prevent the lesion area from expanding.

2. The treatment device of claim 1, wherein the one or more locations are separated by a predetermined gap or more from the boundary of the lesion area.

3. The treatment device of claim 1, wherein the lesion area is any one of an area in which geography angiography has occurred, an area in which drugen is formed, an area in which blood leakage has occurred, and an area in which macular edema is formed.

4. The treatment device of claim 1, wherein the treatment device is for treating ophthalmic disease and the treatment area is located in a patient's fundus.

5. The treatment device of claim 4, wherein the controller controls to radiate the treatment beam along a pattern that partitions between the lesion area and a center of the fundus.

6. The treatment device of claim 4, wherein the treatment beam transfers energy to a depth in which an RPE cell layer is located at a patient's fundus.

7. The treatment device of claim 4, wherein the controller controls to radiate the treatment beam to the one or more locations that are separated by at least one RPE cell size from the boundary of the lesion area.

8. The treatment device of claim 1, wherein the controller controls to radiate the treatment beam in a pattern separated by 10 μm or more from the boundary of the lesion area.

9. The treatment device of claim 1, wherein the controller controls to radiate the treatment beam in a pattern separated by 10-200 μm from the boundary of the lesion area.

10. The treatment device of claim 1, wherein a pattern of the treatment beam encloses the lesion area.

11. The treatment device of claim 10, wherein the pattern of the treatment beam forms a closed curve that encloses the lesion area.

12. The treatment device of claim 1, wherein a pattern of the treatment beam encompasses at least a part of the lesion area.

13. The treatment device of claim 1, wherein the controller controls to radiate the treatment beam to form a first pattern and a second pattern, the first pattern is located outside the lesion area and separated from the boundary of the lesion area, and the second pattern is located further than the first pattern from the boundary of the lesion area.

14. The treatment device of claim 13, wherein a radiation gap of a treatment beam constituting the first pattern is smaller than that of a treatment beam constituting the second pattern.

15. The treatment device of claim 1, wherein the treatment beam includes a plurality of beams, and the controller controls to sequentially radiate the plurality of beams at the same location and controls a parameter of the treatment beam, and
wherein the parameter of the treatment beam is any one of an output, a beam size, and a pulse pattern of the treatment beam.

16. A method of treating a lesion of a patient, the method comprising:
- determining a lesion area using an image of a treatment area comprising the lesion;
- radiating a treatment beam to a plurality of locations adjacent to a boundary of the lesion area so as to prevent the lesion area from expanding,
- wherein the radiating of the treatment beam comprises radiating the treatment beam at the plurality of locations being outside the lesion area and separated from the boundary of the lesion area without radiating the treatment beam to the lesion area.

17. The method of claim 16, wherein the one or more locations are separated by a predetermined gap or more from the boundary of the lesion area.

18. The method of claim 16, wherein the lesion area is any one of an area in which geography angiography has occurred, an area in which drugen is formed, an area in which blood leakage has occurred, and an area in which macular edema is formed.

19. The method of claim 16, wherein the method of treating the lesion is for treating ophthalmic disease and the treatment area is located in a patient's fundus.

20. The treatment device of claim 1, wherein the treatment beam has a wavelength selectively absorbed into an RPE cell layer in a retina tissue, and the wavelength of the treatment beam is in a range of 500 nm-600 nm or 800 nm-900 nm.

* * * * *